United States Patent [19]

Mutzhas

[11] 4,298,005
[45] Nov. 3, 1981

[54] RADIATION APPARATUS

[76] Inventor: Maxim F. Mutzhas, Pilgersheimerstrasse 64, BRD 8000 Munchen 90, Fed. Rep. of Germany

[21] Appl. No.: 55,002

[22] Filed: Jul. 5, 1979

Related U.S. Application Data

[63] Continuation of Ser. No. 773,844, Mar. 3, 1977, abandoned.

[30] Foreign Application Priority Data

Mar. 5, 1976 [DE] Fed. Rep. of Germany ....... 2609273

[51] Int. Cl.³ .......................... A61N 5/00; G01J 1/00
[52] U.S. Cl. ................. 128/396; 250/504 R; 250/510; 313/229; 350/1.6
[58] Field of Search ............... 128/395, 396, 371, 372, 128/373, 374; 250/510, 504, 503; 252/300 IR, 300 UV; 313/486, 229; 350/1.7, 1.6

[56] References Cited

U.S. PATENT DOCUMENTS

| | | | |
|---|---|---|---|
| 1,856,969 | 5/1932 | Reiter et al. | 128/396 |
| 2,016,474 | 10/1935 | Wood | 128/396 |
| 2,339,906 | 1/1944 | Barnes | 250/510 |
| 2,381,451 | 8/1945 | Hrabak | 250/504 |
| 2,461,254 | 2/1949 | Bassett | 250/86 |
| 2,637,322 | 5/1953 | Clay | 128/396 |
| 3,202,811 | 8/1965 | Hall | 362/2 |
| 3,466,443 | 9/1969 | Roesler et al. | 250/504 |
| 3,483,871 | 12/1969 | Wilson | 128/372 |
| 3,590,307 | 6/1971 | Dobrusskin | 313/229 |
| 3,662,175 | 5/1972 | Davidson et al. | 250/510 |
| 3,785,722 | 1/1974 | Schultz | 252/300 G |
| 3,821,577 | 6/1974 | Larson | 313/486 |
| 3,870,873 | 3/1975 | Mallory | 362/2 |
| 4,017,758 | 4/1977 | Almer et al. | 350/1.7 |
| 4,074,164 | 2/1978 | Zeyendecker | 313/229 |
| 4,095,113 | 6/1978 | Wolff | 250/504 |

FOREIGN PATENT DOCUMENTS

| | | | |
|---|---|---|---|
| 1464661 | 2/1969 | Fed. Rep. of Germany | 128/395 |
| 2335423 | 1/1975 | Fed. Rep. of Germany | 250/504 |
| 444915 | 7/1975 | U.S.S.R. | 250/504 |

*Primary Examiner*—Robert W. Michell
*Assistant Examiner*—Arthur S. Rose
*Attorney, Agent, or Firm*—Lockwood, Dewey, Alex & Cummings

[57] ABSTRACT

A radiation apparatus for cosmetic, photobiological and/or photo chemical purposes containing at least one ultraviolet ray source and devices for operation for the production of the ignition voltage and operating current and a filter device for emitting rays in the region of 320 nm to 450 nm and for cutting out short wave rays below 320 nm and long wave rays above 800 nm and preferably above 450 nm.

18 Claims, 5 Drawing Figures

RADIATION APPARATUS

This is a continuation of application Ser. No. 773,844, filed Mar. 3, 1977, now abandoned.

BACKGROUND OF THE INVENTION

This invention relates to a radiation apparatus for cosmetic, photobiological and/or photochemical purposes containing at least one ultraviolet ray source and devices for producing the ignition voltage and the operating current necessary for the operation and preferably including a filter apparatus.

The radiation apparatus is to serve for the treatment of different diseases, for example, psoriasis, hyperbilirubinamie. Furthermore it is to be used for cosmetic purposes for direct tanning.

Also it is used in the field of photo chemistry, for example, for drying of varnishes, for the hardening of plastic and for polymerization.

At present it is known to use in the field of photobiology for medicinal as well as for cosmetic purposes, radiation apparatus with electric ultraviolet ray sources for treatment of different diseases (for example, psoriasis, hyperbilirubinamie) by ultraviolet radiations used in conjunction with medicines. In psoriasis treatment with ultraviolet fluorescent lamps, in which radiation strengths of about 60 $W/m^2$ are used (with 365 nm), there is a psychological disadvantage to the patient because he must be practically shut up in a box. For cosmetic purposes especially in order to achieve the effect of secondary pigmentation (tanning after previous erythema) ultraviolet radiation with a wave length shorter than 320 nm is used.

Furthermore it is known that in solaria light sources of the aforementioned type are used.

As a rule for photochemical purposes, for the drying of varnishes, for the hardening of plastics and for polymerization mercury vapor high pressure lamps are used which emit mixed light in the region of about 250 nm up to, for the tube radiation, several 1000 nm.

Instead of mercury, high or low pressure lamps, the latter for most part with fluorescence, and xenon high pressure lamps are used in such fields. The presently known radiation devices emit to a not inconsiderable extent conjunctivitis- and erythema-active rays, which in wrong dosages, can bring about considerable damage to health. This applies above all to ultraviolet ray sources which operate in the high pressure range. Radiation devices for photobiological purposes equipped with low pressure mercury vapor lamps (fluorescent lamps) are extremely expensive so that they can be used only in clinics and large practices and not for home treatment.

The object of the invention is to provide a radiation apparatus for photobiological and photochemical purposes which supplies in the wave length region of 320-450 nm high radiation strengths and completely suppresses the radiation wave length shorter than 320 nm in order to avoid damage to health by conjunctivitis (inflammation of the conjunctiva) and erythema (sunburn). Furthermore radiation of longer wave length than 450 nm should be substantially suppressed in order to avoid undesired effects on the radiation objects due to high energy loading. To be avoided in particular are dazzling, and damage to the skin by too high radiation loads, the latter particularly in the infra red range.

This problem is solved according to the invention in that the short wave rays below 320 nm are completely suppressed. Discharge lamps which usually are used as ultraviolet ray sources emit the greatest part of their energy in the infra red range. Therefore the infra red rays as of about 800 nm are suppressed as far as possible. In order to reduce the radiation outside the effective range which is between 320 and about 450 nm it is desirable to filter out substantially all the longer wave rays above 450 nm.

An ultraviolet ray source of especially high intensity in the region of 320-450 nm is the mercury vapor high pressure lamps especially those provided with iron iodide and gallium iodide.

In order to obviate the devices connected in series usually necessary for the operation of the mercury vapor high pressure lamp, the lamp may be constructed as a mixed light lamp with the current limitation effected by an incandescent lamp winding.

An ultraviolet ray source which operates as a high or maximum xenon pressure lamp can be intensified in the region of 320-450 nm if it is provided with a metal iodide, preferably iron iodide and gallium iodide.

The short wave rays under 320 nm are suppressed by an ultraviolet edge filter. A very simple ultraviolet edge filter can be produced from plate glass and is usual in the art.

If the temperatures are not too high polyesters also can be used as ultraviolet filters, either in the form of plates or foils. Applying polyester foil directly on the bulb or tube of the fluorescent lamp insures that no rays under 320 nm emerge.

The radiation load in the visible range above 450 nm can be achieved by the use of color filters, preferably a blue violet filter. This filter may consist of glass, quartz or plastics in which finely divided heavy metal oxides, for example, cobalt, nickel, iron-oxide are dispersed or deposited on the surface.

A color filter made from the violet glass may be placed over the burner of the high pressure lamp. It also serves as a protective tube for the sensitive burner quartz tube. If cobalt oxide is added to the fused quartz, the burner tube itself may serve as a blue violet filter whereby with suitable proportioning of the amount added, ultraviolet filtering in the region below 320 nm can be achieved.

In the radiation procedure an infra red filter may be inserted between the ultraviolet ray source and the radiation object which may act either as an absorption or reflection filter.

The simplest solution of this type is to use a heat absorptive glass, usual in the art, as an infra red filter. Instead of the maximum necessary three filter types, a single filter may fulfill the three functions if, for example, the corresponding additional materials for the color filtering and/or infra red filtering are added to the plate glass fusion in suitable quantities. The same applies if instead of the plate glass fusion a quartz fusion is used or the filter materials are finely divided in plastics or deposited on the surface.

The housing in which the ultraviolet ray source is located is produced either from polished oxidized aluminum or it contains reflectors from this material in order to increase the radiation output.

For cooling of the housing ventilation openings with shield plates are provided so that no unfiltered rays can emerge from the housing. The arrangement of these inlet and outlet openings is such that the ray source, the housing and the filters are sufficiently cooled.

For increasing the cooling effect a ventilator is provided in order to carry out the cooling more effectively.

The cooling of ultraviolet ray source and/or housing is suitably regulable or adjustable. This gives an optimum operating temperature for the housing and lamp. The housing must not be too hot because of the added devices and the danger of burns to operator of the radiation apparatus.

The cooling may be effected by means of a ventilator and/or a blower, regulated or adjusted by electrical means.

Advantageously the cooling is controlled so that the ultraviolet ray source is not cooled during ignition. Thus, an optimum operating temperature of the burner results; if the space between the burner and the protective tube upon starting the lamp is completely cooled, the optimum operating temperature of the burner is not obtained.

The cooling is suitably regulated by an electronic delay switch which preferably also monitors the temperature of the ultraviolet ray source and/or housing.

In order to obtain as high an ultraviolet ray output as possible the temperature at the wall of the burner must not fall short of a certain minimum value. On the other hand, it is important that at the place where the current leads to the electrode are embedded a maximum temperature must not be exceeded if the lamp is not to burn out prematurely.

The exhaust cooling air may be discharged outside the room.

Radiation devices of extremely high outputs containing several ultraviolet ray sources will heat up the room excessively if the exhaust air from cooling remains in the room.

At least one additional ultra violet ray source which emits erythema-effective rays is included. It may be operated continuously or intermittently by impulse switching.

Advantageously the ignition device is switched off after the ignition of the ultraviolet ray source.

The ignition, which requires higher voltages than the usual line voltages, is effected either by resonance switchings, transformers or high frequency ignition devices which consist of spark sections and windings. After ignition with a high frequency device the full lamp current flows through the windings. Therefore the windings must be dimensioned correspondingly thick. If the ignition device is switched off after the ignition of the ultraviolet ray source considerable saving in cost, weight and space can be achieved.

The current drawn by the radiation device is of such magnitude that current plugs used for normal domestic current circuits will suffice. Thus the radiation apparatus can be used as a home radiation apparatus.

Also in order to be able to carry out home radiations it is necessary to design the electrical parts of the radiation apparatus so that they will operate on standard house voltage and current. This means that the lamp-burning voltage must amount to a maximum of $\frac{2}{3}$ the line voltage of the power supply and must be properly fused so as not to exceed the maximum line current. On the other hand the highest possible output of the ultraviolet ray source (lamp) is necessary in order to achieve the best possible effect in the shortest time.

The space between the burner bulb and protective tube may be cooled by air preferably supplied from the previously-described ventilator. The air cooling if necessary may be supplemented or replaced by suitably-arranged water cooling. Care must be taken that liquid coolant does not contact the burner, since a mercury vapor high pressure lamp for example operates at a temperature between 700° and 900° C.

Special advantages of the radiation apparatus of the invention are:

Avoiding of conjunctivitis and erythema by the filtering out of the rays below 320 nm, which rays according to the literature have a carcinogenic effect.

By filtering out the infra red radiation the heat loading of the radiation object is considerably reduced so that even with very intensive radiation no heat erythema results. With a pigmenting effective radiation strength of about 150 W/m², a total radiation loading of about 2500 W/m² would result if the infra red and visible-light portions are not filtered out. If these wave lengths are filtered out this value is reduced by about 80%.

Due to the blue violet filter the luminous density of the light source is reduced so markedly that any permanent dazzle phenomena is eliminated.

The use of gallium iodide and iron iodide increases the radiation output of the high pressure discharge in the range of 320-450 nm by a considerable amount. If the mercury vapor high pressure lamp is constructed as a mixed light lamp the added device is dispensable and the lamp can be operated directly on standard power supply.

Ultraviolet edge filters made from plate glass known in the art are extraordinarily cheap. The same applies to filters from polyesters. If a blue violet glass tube is used as the color filter, this results in a considerable reduction in cost compared with blue violet filter discs.

One of the most important advantages however is that radiation wave lengths between 320 nm and 450 nm can now be achieved cheaply in practice. This applies to photobiology as well as also to photo chemistry.

The invention will be described with reference to the accompanying drawings.

Figure 1:
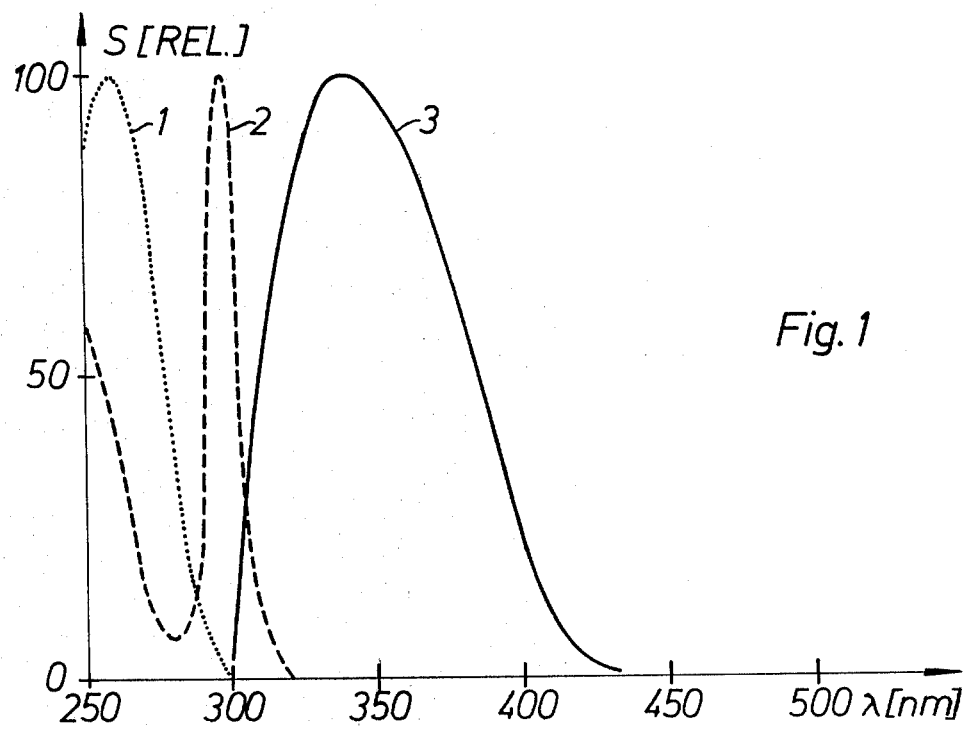
FIG. 1 shows three photobiological effective curves $S=f(2)$.

In FIG. 1 the conjunctivitis sensitivity 1, the erythema sensitivity 2 and the spectral effect curve of the direct pigmentation 3 is shown in relative scale.

The maximum for the sensitivity of the photo conjunctivitis is about 260 nm; the dose threshold value corresponding to this wave length is about 50Ws/m².

The maximum of the erythema sensitivity is about 297 nm; the dose threshold value with this wave length amounts to about 100,000 Ws/m².

Figure 2:
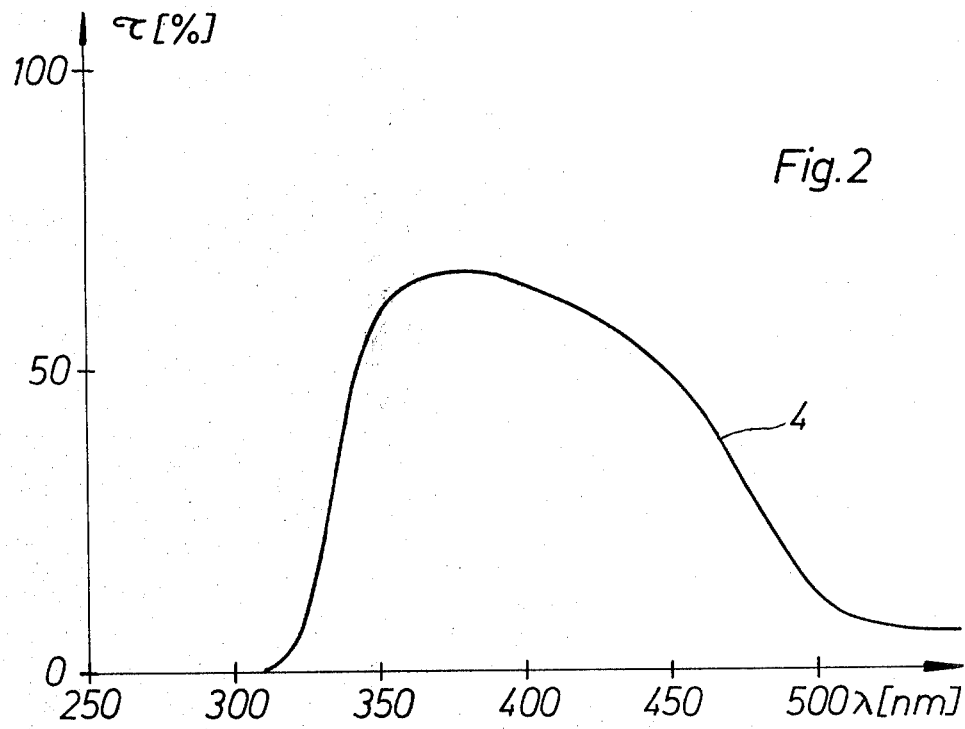
FIG. 2 shows the spectral curve for the transmission rate of a filter device $\tau=f(2)$.

FIG. 2 shows the spectral curve of the transmission values 4 of a filter device which consists of an ultraviolet edge filter (plate glass 5 nm), an infra red absorption filter (heat absorption glass 4 nm) and a color filter (blue violet glass 1 nm). In the range (not shown) from about 600 nm to the far infra red the transmission value is about 6%.

Figure 3:
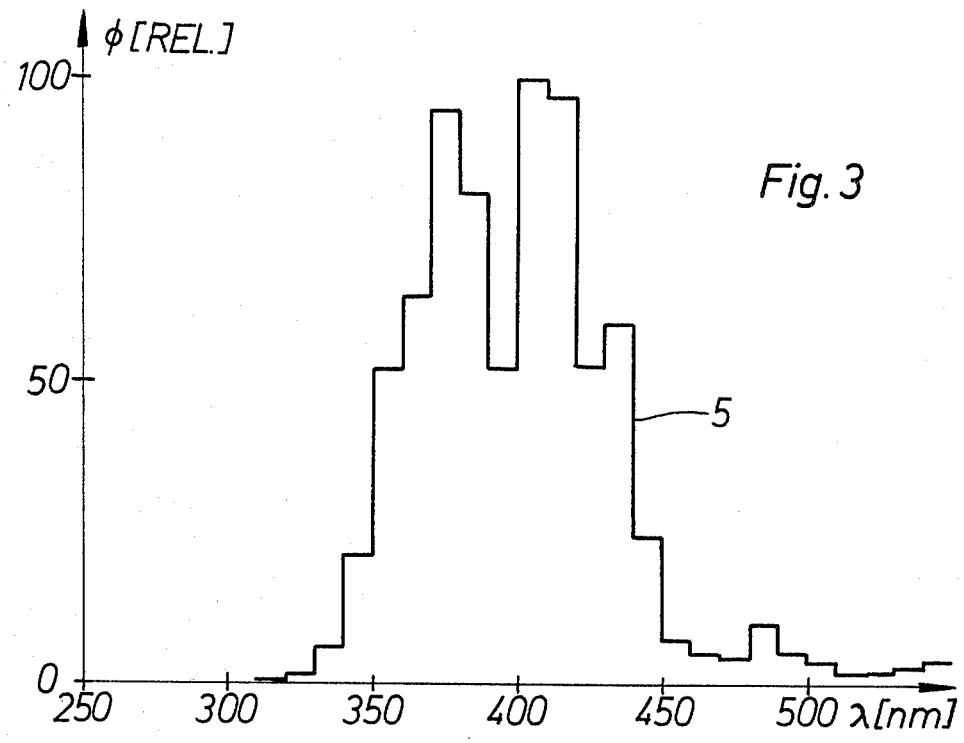
FIG. 3 shows the spectral radiation output of a mercury vapor high pressure lamp with filter device $\phi=f(2)$.

In FIG. 3 is shown the spectral ray output distribution of a 2000 W mercury vapor high pressure lamp with the filter device of FIG. 2 as a discontinuous curve 5 in relative scale. Each of the measurements were taken within a band width of 10 nm.

Figure 4:
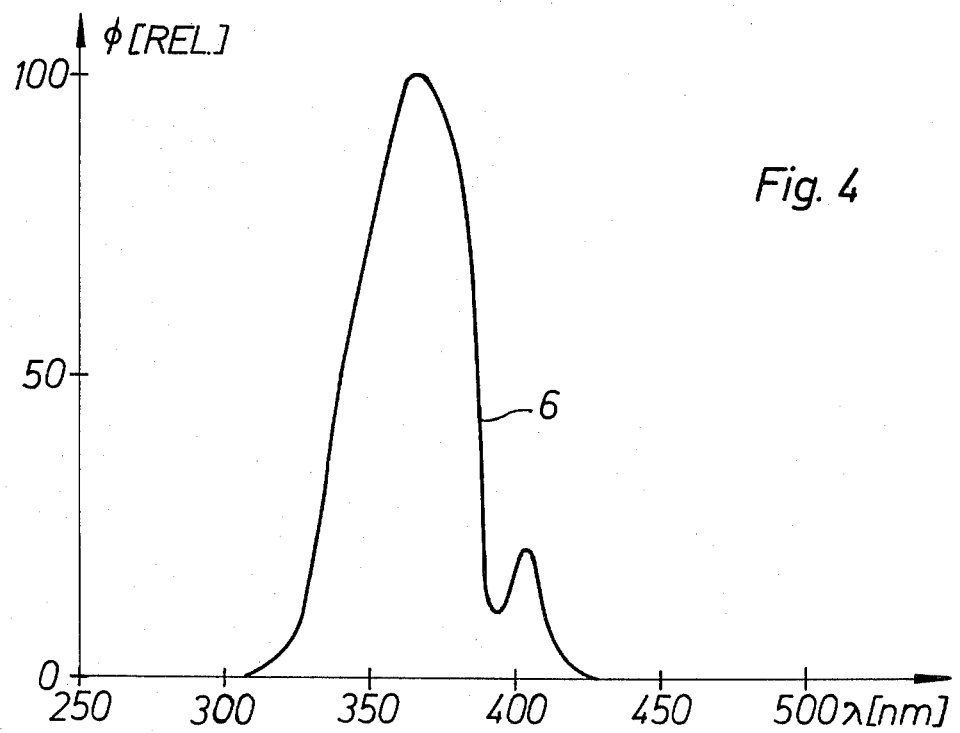
FIG. 4 shows the spectral radiation output of an ultra violet fluorescent lamp with polyester filter $\phi=f(2)$.

FIG. 4 shows the spectral radiation output distribution of a 40 W fluorescent lamp with lead-activated barium disilicate, surrounded with a covering of 0.175 nm thick polyester foil as a curve 6 in relative scale.

Figure 5:
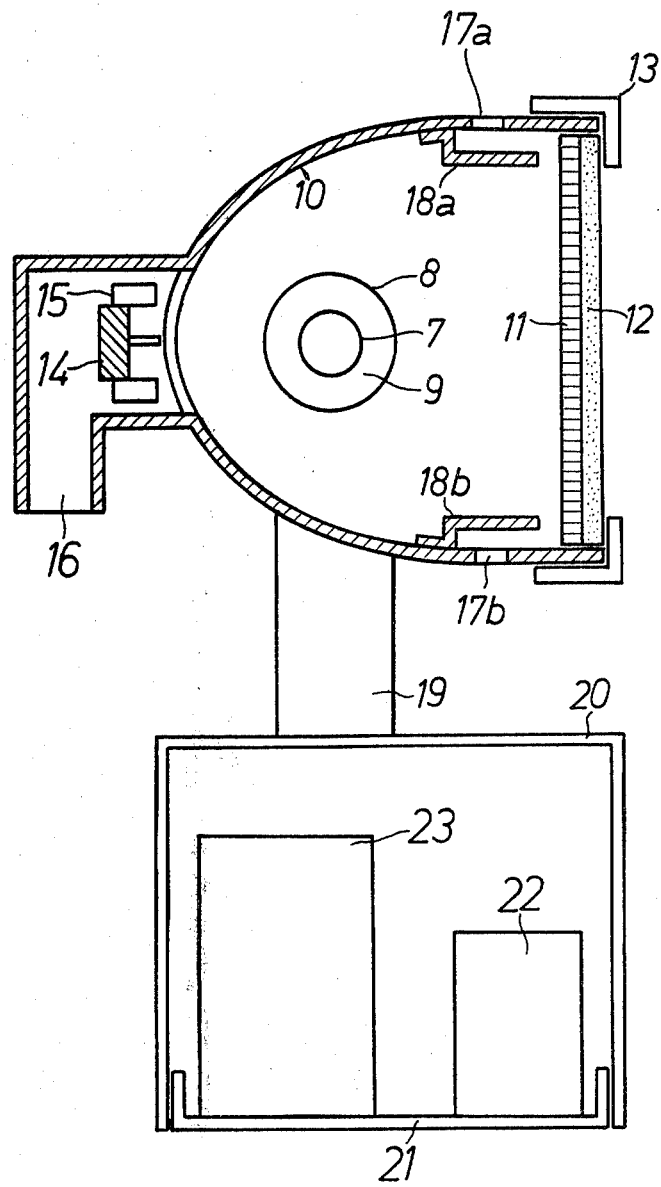
FIG. 5 shows one embodiment of a radiation apparatus.

In FIG. 5 is shown one embodiment of a radiation apparatus with an ultraviolet ray source 7 surrounded with a protective glass tube 8 which serves as a filter. The space 9 between the burner tube 7 and protective tube 8 may be evacuated for thermal reasons.

The inside of the housing 10 serves as a reflector. The heat absorption disc frame 11 and the residue ultraviolet absorber 12 are held together by the frame. The ventilator motor 14 with its ventilator vanes 15 draw the air through the inlet duct 16 and forces it past the lamp and through the surrounding space. The exhaust air escapes through the openings 17a and 17b. The shield plates 18a and 18b prevent the escape of any unfiltered rays. The support frame 19 fixed preferably on both sides permits the lamp housing 10 to pivot over a predetermined range. The frame 19 is attached to the additional apparatus housing 20, the bottom plate 21 of which carries an ignition device 22 and the impedance coil 23.

If a 2000 W mercury vapor lamp containing metal iodide is used as a ray source, a suitable color filter comprises a glass tube 40 mm in diameter and 1 mm wall thickness to reduce significantly the light density of the lamp. For reasons of cost the use of ultraviolet or blue glass discs is not recommended as the prices for these are so extremely high that the device may not be practical economically.

As a heat protection filter it is proposed to use heat absorption glass usual in the art, which in the region of 800 nm (long infra red wave lengths) has a transmission value of only 6%. Possible residues of ultraviolet radiation, which is shorter than 320 nm, can be removed by ultraviolet edge filters which, similar to the blue violet glasses, are relatively expensive. The most effective solution economically is normal plate glass which likewise acts in this area as an edge filter.

Such a radiation apparatus produces effective pigmentation radiation strengths in the order of magnitude of over 150 W/m$^2$ (comparison value for unfiltered sun radiation with 90° sun altitude is about 50 W/m$^2$). From this it follows that after a radiation exposure time of about ten minutes the threshold value for direct tanning is achieved (comparison value for the unfiltered sun radiation at 90° sun altitude is about thirty minutes). The total radiation strength when the radiation apparatus is provided with a ventilator of ample size amounts to about 500 W/m$^2$ (comparison value for unfiltered sun radiation at 90° sun altitude is about 1100 W/m$^2$).

The erythema threshold would be achieved purely mathematically after about seven hours, a value which cannot be checked experimentally (comparison value for the unfiltered sun radiation at 90° sun altitude is about four minutes). By using appropriate dosages of methoxy psorales (preferably 0.75 to 1.5% 8-MOP solution or the corresponding internal application of this medicine), the threshold time for the direct tanning by sensitising of the skin can be reduced considerably.

A similar sensitising may be effected by erythema-effective ultraviolet radiation, for example, by short time removal of the plate glass 12, this radiation being under the erythema threshold; or by additional ultraviolet ray sources which are operated continuously or upon impulse operation.

What I claim is:

1. In a radiation apparatus for cosmetic, photobiological and/or photochemical purposes comprising,
   housing means having an opening therein,
   at least one ultraviolet ray source in said housing means and positioned to direct its rays toward and through said opening, said ray source comprising a mercury vapor high pressure lamp containing a metal halogen vapor which lamp produces radiation of substantial intensity in the wavelength range of 320–450 nm,
   reflector means formed of a material having a high reflectance for radiation in the wavelength range of 320–450 nm for reflecting the radiation produced by said ray source, said reflector means comprising said housing means and said material comprising polished oxidized aluminum,
   filter means for completely suppressing all short wavelength rays passing through said opening having wavelengths below approximately 320 nm, and for suppressing longer visible wavelength rays passing through said opening having wavelengths above approximately 450 nm, and
   cooling means for cooling said housing and said source during operation, said cooling means comprising ventilator means for ventilating said housing,
   the aforementioned components of said apparatus coacting in combination with each other to result in the production of radiation in the wavelength range of 320–450 nm of at least 150 W/m$^2$.

2. A radiation apparatus according to claim 1, characterized in that the mercury vapor high pressure lamp is constructed as a mixed light lamp.

3. A radiation apparatus according to claim 1, characterized in that said filter means includes an ultraviolet edge filter made from plate glass.

4. A radiation apparatus according to claim 1, characterized in that said filter means includes an ultraviolet edge filter comprising polyester plates or foils.

5. A radiation apparatus according to claim 4, characterized in that the polyester foil is deposited directly onto the surface of the lamp.

6. A radiation apparatus according to claim 1, characterized in that said filter means includes a color filter from the group consisting of glass, plastics and quartz carrying a finely-divided heavy metal oxide taken from the group consisting of cobalt oxide, nickel oxide and iron oxide.

7. A radiation apparatus according to claim 1, wherein said ultraviolet ray source includes a burner tube covered with a color filter tube.

8. A radiation apparatus a-cording to claim 1, wherein said ultraviolet ray source includes a burner tube constructed as a high pressure color filter tube made of quartz containing cobalt oxide.

9. A radiation apparatus according to claim 1, characterized in that said filter means includes an infrared filter comprising a heat filter.

10. A radiation apparatus according to claim 9, characterized in that said infrared filter comprises a heat absorption glass.

11. A radiation apparatus according to claim 1 wherein said filter means comprises a single filter device which performs simultaneously the functions of an ultraviolet edge filter and an infrared filter.

12. A radiation apparatus according to claim 1, characterized in that said housing is provided with ventilation openings shielded to prevent emergence of unfiltered rays therethrough.

13. A radiation apparatus according to claim 1 in which said ultraviolet ray source comprises a burner tube and a surrounding protective tube, the space therebetween being evacuated.

14. A radiation apparatus according to claim 1 in which said ultraviolet ray source comprises a burner tube and a surrounding protective tube, the space therebetween being cooled by fluid flowing through.

15. A radiation apparatus according to claim 14, characterized in that the cooling is effected by a blower.

16. A radiation apparatus according to claim 1, which includes an ignition device for said ultraviolet ray source and switch means to turn off said ignition device after the ignition of the ultraviolet ray source.

17. A radiation apparatus according to claim 1, wherein said metal is selected from the group consisting of iron, gallium and mixtures thereof.

18. A radiation apparatus according to claim 1, characterized by the fact that said mercury vapor high pressure lamp has a capacity by which a pigmentation effecting radiation strength results which is greater than three times that of the unfiltered radiation of the sun positioned at 90° elevation.

* * * * *